United States Patent
Shields

[11] Patent Number: 5,401,250
[45] Date of Patent: Mar. 28, 1995

[54] TETHERED CONICAL SHIELD FOR PHLEBOTOMY NEEDLES

[76] Inventor: Jack W. Shields, 1950 Las Tunas Rd., Santa Barbara, Calif. 93103

[21] Appl. No.: 134,178

[22] Filed: Oct. 7, 1993

Related U.S. Application Data

[63] Continuation-in-part of Ser. No. 956,790, Oct. 5, 1992, abandoned.

[51] Int. Cl.⁶ ............................................. A61M 5/32
[52] U.S. Cl. ................................. 604/192; 604/263
[58] Field of Search ............... 604/192, 198, 187, 263, 604/110, 177, 163; 206/365, 366

[56] References Cited

U.S. PATENT DOCUMENTS

| | | | |
|---|---|---|---|
| 4,932,946 | 6/1990 | Shields | 604/263 X |
| 4,943,283 | 7/1990 | Hogan | 604/263 X |
| 5,061,250 | 10/1991 | Shields | 604/263 X |
| 5,112,311 | 5/1992 | Utterberg et al. | 604/192 X |

Primary Examiner—John D. Yasko

[57] ABSTRACT

I describe a puncture-resistant hollow cone with a leading tether, a slanted leading aperture and a trailing bore of decreasing diameter for shielding and preventing accidental injuries from a hollow-bore steel needle after use for giving an intravenous (IV) infusion or withdrawing blood through trailing tubing. When the puncture-resistant hollow cone is slid over trailing tubing to overlie the needle hub, and the tether is held down with one finger over a venipuncture site, the other hand retracts trailing tubing attached to the needle hub until the trailing end of the needle hub becomes wedge impacted in the trailing bore of the puncture-resistant hollow cone, leaving the needle shaft and tip safely shielded within the leading bore of the puncture-resistant hollow cone in a space inaccessible to a user's finger.

6 Claims, 3 Drawing Sheets

TETHERED CONICAL SHIELD FOR PHLEBOTOMY NEEDLES

This application is a continuation-in-part of Ser. No. 07/956,790, filed Oct. 5, 1992, now abandoned.

BACKGROUND OF THE INVENTION

1. Field of the Invention

This invention relates to the prevention of accidental hollow-bore needle-stick injuries whereby health car workers can become infected with blood-borne pathogens, including human immunodeficiency virus (HIV), hepatitis B virus (HBV) and hepatitis C virus (HCV), during and after withdrawal of hollow-bore steel IV access needles having rigid round or soft rectangular hubs permanently attached to trailing tubing.

2. Description of Prior Art

To prevent needle-stick injuries to health care workers, puncture-resistant cylinders which slide over syringes to extend beyond the tip of an injection needle and,- then, lock by mechanical means are now produced by Becton-Dickson and Sherwood Medical Corporations. Similar open-ended shields which slide over the trailing tubing in infusion assemblies and blood collecting devices have been described, but are not in common use. However, such shields are crucial in preventing needle-stick injuries to health care workers, because phlebotomy needles are customarily inserted into veins and, therefore, customarily hold blood in their bores during and after withdrawal.

The use of tethers as parts of needle shields have been described by Slaughter (U.S. Pat. No. 4,781,697—Nov. 1, 1988), Dombrowski et al (U.S. Pat. No. 4,790,828—Dec. 13, 1988), Corey (U.S. Pat. No. 4,955,866—Sep. 11, 1990), and Simon (U.S. Pat. No. 5,051,109—Sep. 24, 1991). None of these describe a tether which uses an IV access site in a patient for an anchor.

In U.S. Pat. No. 4,932,946, issued Jun. 12, 1990, Shields described a tab 11 on the leading end of a slit elastomeric robe containing a cylindrical needle shield for safely exposing and recapping the tip of a hollow-bore steel needle attached to a standard syringe. This invention is pertinent, but not applicable because syringes lack trailing tubing.

In U.S. Pat. No. 5,061,250, issued Oct. 29, 1991, Shields described a tether with a tab finger-held over a vein in order to pull a slit elastomeric tube containing a puncture-resistant cone over a needle during withdrawal. This invention, incorporating a tether 16 with an attached tab 17 and a trailing cone 13 is pertinent to the the instant invention, but not directly applicable because effective use depends on the inclusion of a slit elastomeric tube attachable to the hub of an IV infusion needle with trailing silastic robing.

In U.S. Pat. No. 5,197,956, issued Mar. 30, 1993, Brizuela described a slotted puncture-resistant cylinder with a beveled trailing ring 7 which can slide over Wailing tubing attached to a serum bag to safely entrap a leading cannula by means of a protrusion 12 of trailing tubing over its attachment to the cannula hub 10. He described a cap 8 with a tether 9 for closing the leading end of said cylinder after the cannula is withdrawn. He did not describe a leading tether or tab for stabilizing this cylinder over a venipuncture site.

In U.S. Pat. No. 4,943,283, issued Jul. 24, 1990, Hogan described two hollow cylinders 30,40 concentrically added during assembly to prevent needle-stick injuries from phlebotomy sets having hollow-bore steel needles on each end of segmented silastic tubing. In a second preferred embodiment, the tubing permanently attached to the IV access needle is supplied with such a cylinder. Hogan does not include a leading tether, tab or a trailing cone for wedge-impacting the trailing end of a round or rectangular needle hub. Instead, the device depends on adding a wedge-like detent 43 on the leading end of the trailing tubing 14 to prevent forward motion of the needle hub after its trailing portions of least diameter have been retracted through a series of radial slits 53 in a cupped trailing end of the cylinder 40.

In U.S. Pat. No. 5,112,311, issued May 12, 1992, Utterberg and Sheehan described a puncture-resistant cylinder 1 with a leading tether 122, a tab 124 and paired slots 1c which slide together over the hub 3 of a winged infusion assembly to safely enclose the infusion needle 5 after use. They described use of the tether and tab for anchoring the cylinder with respect to an IV access site during needle withdrawal. (See FIG. 14). However, withdrawal, forward and backward excursion of the tethered puncture-resistant and slotted cylinder is limited to the length of wing attachment to the needle hub, especially when said assembly is supplied, as claimed, as a surrounding attachment to a the hub of a winged infusion needle assembly. This invention applies only to winged infusion assemblies, and is structurally inapplicable to IV infusion needles having round or rectangular trailing hubs of small diameter lacking "butterfly" wings.

In U.S. Pat. No. 5,085,639, issued Feb. 4, 1992, Ryan teaches use of a stepped hollow cylinder within the body of a winged infusion assembly for safely trapping a retracted infusion needle having a hub with shoulders matching the steps. He did not teach the use of a leading tether for anchoring the winged body during retraction of the leading hollow-bore steel needle, or the use of a simple cone to wedge-impact the trailing end of the hub which holds and stabilizes the needle during IV insertion and retraction.

In U.S. Pat. No. 4,935,011, issued Jun. 19, 1990, Hogan taught use of a flat envelope into which an IV access needle attached to a winged infusion can be safely withdrawn, part of said envelope comprising a compression flap adapted to overlie the venipuncture site while the needle is being withdrawn from a patient's vein. This patent does not include the use of cylindrical or conical shields for needle protection, and is applicable only to winged or "butterfly" infusion assemblies attached to Wailing tubing.

In U.S. Pat. No. 5,176,657, issued Jan. 5, 1993, Shields described a hollow conical shield used to first contain a fluid-filled cartridge and, used later, a to wedge impact the leading end of a rigid dental syringe into which this cartridge is breech-inserted, so that the leading tip of hollow-bore steel needle is always protected before, between uses and after use for giving dental anesthesia. This patent is cogent, because it teaches the use of a hollow cone to wedge impact the leading end of a rigid syringe into a confined puncture-resistant space wherein a leading hollow-bore steel needle can be held and manipulated safely. However, this patent does not embody, include or necessitate the use of a tether for safe usage.

The use of matching hollow cylinders or cones with solid cones of decreasing diameter to create wedge impactions is common practice with respect to the leading ends of needle hubs inserted into needle shields or sheaths supplied with disposable hollow-bore steel needles. However, the use of a hollow cone to wedge impact the trailing end of a round or rectangular needle hub of an IV access needle attached to trailing tubing is novel in the prevention of needle-stick injuries. The attachment of leading tethers to such hollow conical shields is novel, except as claimed in Shields' U.S. Pat. No. 4,932,946, along with slanting of the leading large apertures and constriction of trailing apertures, as described below.

SUMMARY

The object of this invention is to provide and teach novel methods whereby health care workers can withdraw hollow-bore steel needles from the veins of patients without exposing the points after use for giving infusions or withdrawing blood.

Another object is to provide assemblies for withdrawing blood or giving IV infusions which can be handled like counterparts commonly used, without encumbrance of the needle/hub parts from bulky apparata intended to prevent accidental needle sticks.

A third object is to provide equipment which is simple, reliable, efficient and easy to use with both hands kept in safe positions during and after needle withdrawal.

A fourth object is to protect by-standers and personnel responsible for the disposal of tubing with needles still attached.

A final object is to provide a needle safety system which can be manufactured easily, inexpensively and put to critical care use almost immediately, when applied to phlebotomy and intravenous infusion equipment with trailing silastic tubing. (See Drawings).

DESCRIPTION OF PREFERRED EMBODIMENTS

Figure 1:
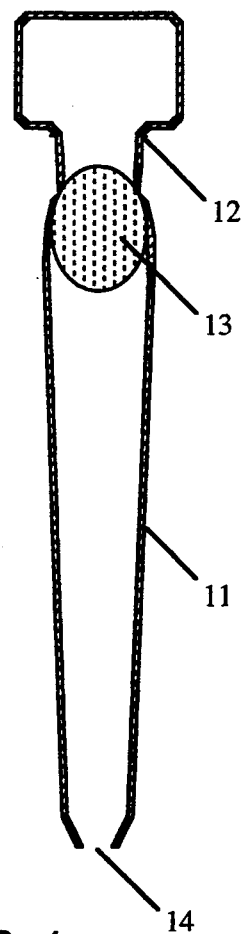
FIG. 1 is a diagrammatic ventral view of a hollow conical shield with a leading tether, a slanted leading aperture of large bore and a trailing aperture of small bore. (Scale 1:1).

A first preferred embodiment of the hollow conical needle shield is shown in FIGS. 1,3 and 4–9. As shown in FIG. 1, a hollow puncture-resistant cone 11 is molded from semi-rigid, preferably clear, plastic material to comprise a leading tether 12, a slanted aperture of large bore 13, an elongated conical body 11, and a trailing aperture of small bore 14.

Figure 3:
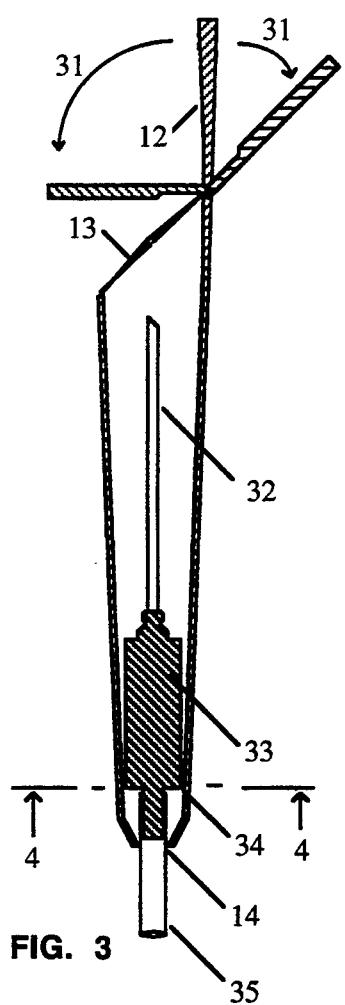
FIG. 3 is a diagrammatic side view rotated 90° to the fight from FIG. 1, showing the potential arc of tether excursion, the leading aperture at a right angle, and the hub of a phlebotomy needle wedge impacted in the Wailing bore of the hollow conical shield.

As shown in FIG. 3, the leading tether 12 flexes or extends over the leading slanted aperture 13 in an arc 31 of 135° or more in order to put finger pressure over a venipuncture site, to anchor the leading end of the hollow cone 11, and provide optimal orientation of the leading slanted aperture 13 and trailing hollow cone 11 during withdrawal of a hollow-bore steel 32 from the vein of a patient. The least diameter of the slanted aperture 13 in the leading part of the hollow cone 11, is substantially larger than the greatest diameter of the hub 33 of the needle 32; while the least diameter in the trailing bore 34 of the hollow conical shield 11 is smaller than the greatest diameter of the trailing part of the needle hub 33. The trailing aperture 14 in the cone has a diameter equal to or slightly smaller than the external diameter of the trailing tubing 35 permanently attached m the needle hub 33.

Figure 4:
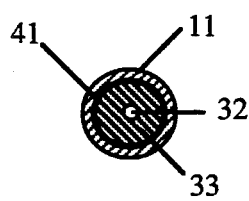
FIG. 4 is cross sectional view taken along line 4—4 in FIG. 3, showing the impaction of a rigid round needle hub within the trailing bore of the conical needle shield.

As shown in FIG. 4, from cross section 4—4 in FIG. 3, if the largest trailing diameter of the needle hub 33 is equal all around, the hub will become circumferentially wedge impacted 41 within the hollow cone by a force proportional to area of surfaces making contact, and proportional to the retractive force exerted to pull a solid cylinder into a hollow cone of smaller diameter. Because the hubs of needles or Luer-Loks for holding needles are usually rigid, compared with semi-rigid plastics used to make needle shields, the surface areas wedge impacted 41 will depend on differential elasticity, as well as retractive force.

Figure 5:
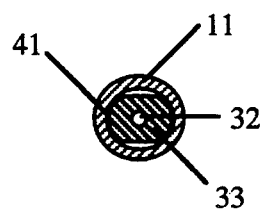
FIG. 5 is cross sectional view taken along line 4—4 in FIG. 3, showing the wedge impaction of a soft rectangular needle hub in the conical needle shield.

As shown in FIG. 5, also from cross section 4—4 in FIG. 3, if the largest trailing diameter of the needle hub 33 is not equal all around, as is the case with respect to large, but soft rectangular and multi-angular needle hubs commonly used in blood banks and plasma collection centers, one can expect the softer elastomeric hub material to compress with forced retraction into a relatively rigid cone; and, thus, increase surface area wedged in mutual contact 41, as depicted by contact line thickness in FIGS. 4–5.

Figure 6:
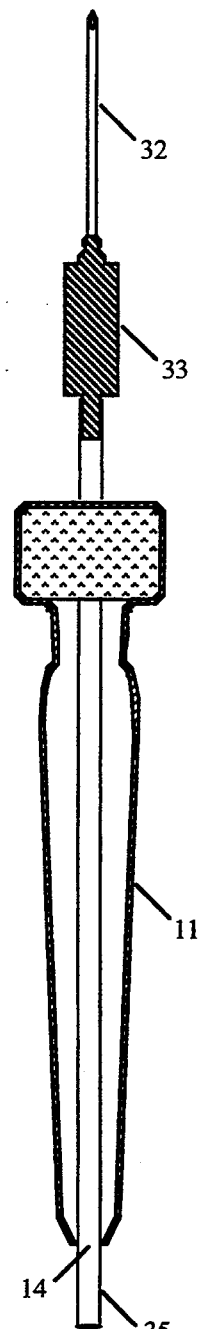
FIG. 6 is a diagrammatic dorsal view, showing the hollow cone of FIG. 1 applied over the trailing tubing in a phlebotomy assembly, and showing a roughened surface on an expanded dorsal surface of the leading tether.

As shown in FIG. 6 the hollow conical shield 11, when applied over trailing tubing 35, resides significantly behind the IV access needle 32 and its hub 33. How far behind depends on trailing attachments to the tubing. In the case of standard phlebotomy equipment, blood plasma collecting and dialysis assemblies, trailing attachments usually vary from 12–72" behind the needle hub 33. This distance leaves ample room to use the leading needle, hub and trailing tubing customarily without encumbrance from bulky equipment. With tight fitting of the trailing aperture 14 over the tubing 35, or alternative means for restraining forward motion, the hollow cone 11 will remain sufficiently remote to not encumber the hub/needle assembly during intended use for phlebotomy.

Figure 7:
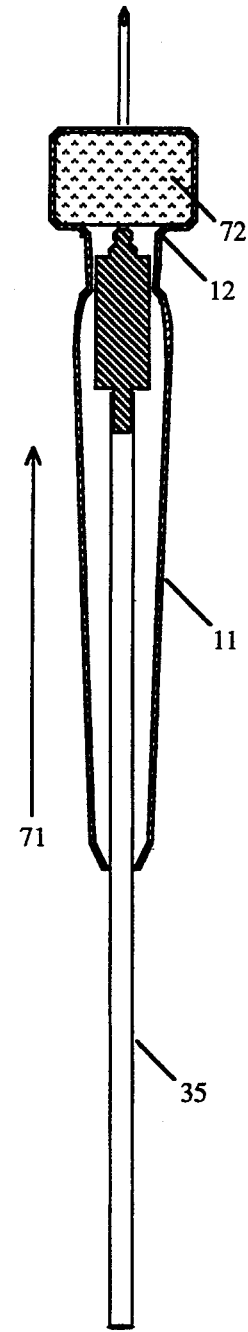
FIG. 7 is a diagrammatic dorsal view, showing the hollow cone advanced over trailing tubing until the roughened portion of the leading tether overlies a venipuncture site.

As shown in FIG. 7, when the time comes to remove the needle 32 from a vein, the hollow conical shield 11 is manually displaced forward over the trailing tubing 35 in the direction of the arrow 71, until a broad toughened dorsal surface 72 on the leading tether 12 overlies the venipuncture site.

Figure 8:
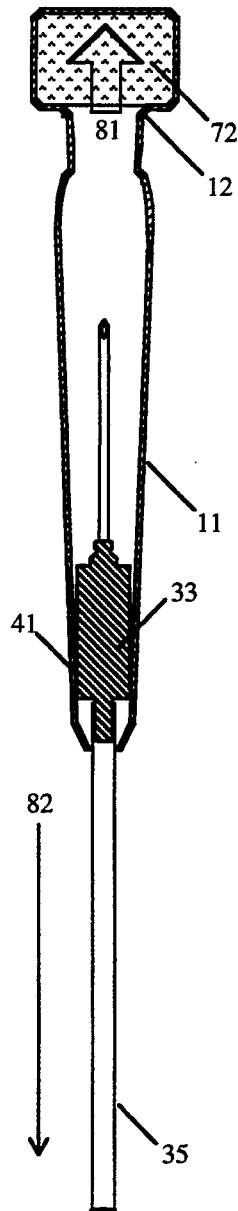
FIG. 8 is diagrammatic dorsal view, showing the hub, shaft and point of the phlebotomy needle retracted by pulling on trailing tubing to the point of wedge impaction of the needle hub in the trailing bore of the hollow conical shield.

As depicted in FIG. 8, downward pressure indicated by the arrow 81 on the roughened surface 72 of the leading tether 12, coupled with backward traction on the trailing tubing 35 in the direction of the arrow 82, will pull the needle hub 33 back into a wedged impaction 41 in the trailing bore of the hollow cone 11, as depicted in the descriptions of FIGS. 3-5.

Figure 9:
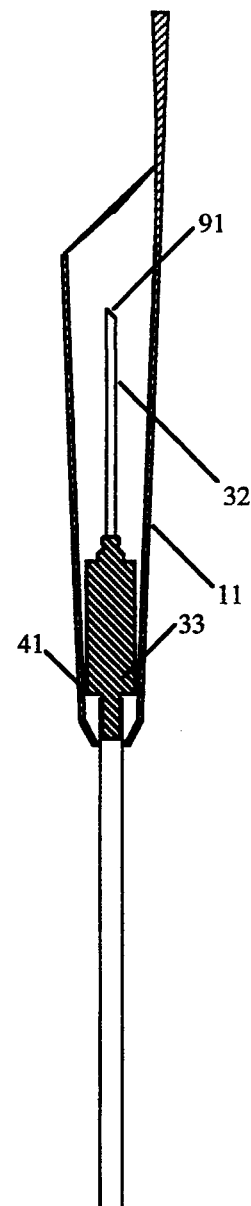
FIG. 9 is a diagrammatic side view, rotated 90° to the right from FIG. 8, showing the hub, shaft and needle tip safely enclosed inside the hollow conical needle shield.

Finally, as shown in FIG. 9, when the needle hub 33 is safely wedge impacted 41 in the trailing bore of the hollow cone 11, the sharp tip 91 and shaft of the hollow-bore steel IV access needle 32 will reside in an enclosed space within the bore of the hollow conical shield 11. Then, the assembly can be safely disposed into a sharps container.

Figure 2:
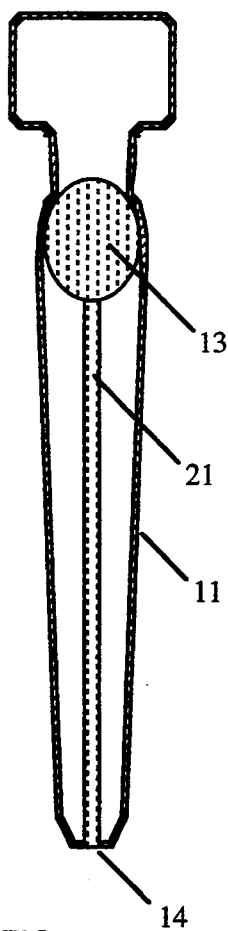
FIG. 2 is a diagrammatic ventral view as in FIG. 1, showing a ventral slot for slipping the hollow cone over IV tubing trailing a needle hub.
Figure 10:
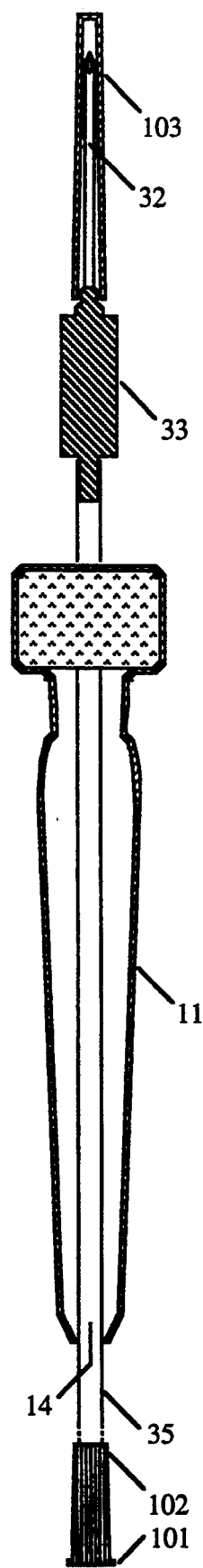
FIG. 10 is a diagrammatic dorsal view, simailar to FIG. 6, showing a trailing hub permanently affixed to the trailing tubing and a needle sheath temporarily attached to the leading hollow bore steel needle.

In a second preferred embodiment shown in FIG. 2, the hollow conical shield 11 is molded such that a ventral slot 21 extends from the large bore of the slanted leading aperture 13 to the trailing small bore aperture 14 of the cone 11. This embodiment of the conical shield has the advantage that it can be applied by the user over trailing tubing in standard existing phlebotomy and IV infusion assemblies with largetrailing hubs or bags already attached by the manufacturer, either before use for phlebotomy or just before the IV access needle is withdrawn. Subsequent manipulation is as described above in relation to FIGS. 1,3,4,5,6, 7, 8,9. The second preferred embodiment has disadvantages in that:

1. It will not be supplied attached to original equipment and, therefore, might not be used under a variety of circumstances where protection from needle-sticks is prudent.
2. It might not be as stable as the first preferred embodiment, owing to alterations in elastic coefficients created by the slot. However, choices in material rigidity and thickness, especially in the Wailing end of the hollow cone 11 can overcome this disadvantage. In a third preferred embodiment shown in FIG. 10, the trailing aperture 14 in the hollow conical shield 11 is constituted with an internal diameter slightly larger than the greatest external diameter of the trailing flange 101 on a hub 102 permanently affixed to the trailing tubing 35 and smaller than the greatest external diameter of the needle hub 33 enclosing the leading hollow bore steel needle 32. The greatest external diameter of a flange customarily affixed to hub on the trailing end of silastic tubing commonly used for conveying blood or IV infusions usually measures 0.773 cm. at the apogee of the flange. This embodiment permits the user to attach the tethered hollow conical shield 11 over a standard phlebotomy or an IV infusion assembly before customary use, immediately after the customarily supplied needle sheath 103 is manually removed.

To operate the first and second embodiments of the hollow conical shield 11,21, the user first employs the IV infusion or phlebotomy assembly customarily. When the infusion or phlebotomy is completed, a right-handed user places a sterile pledget over the site of needle entry into the skin and manually displaces the hollow cone 11 forward over the trailing tubing 35, until the broad roughened dorsal surface 72 of the tether 12 overlies the pledget, venipuncture site and site of skin entry. Downward pressure 81 exerted by the thumb or forefinger of the left hand over the roughened dorsal surface 72 of the tether 12 will temporarily occlude the vein and provide a leading anchor for the hollow cone 11. With the leading part of the tether 11 so anchored, traction exerted by the right hand on the trailing tubing 35 in line with the path of needle entry will cause the needle tip 91, shaft 32 and hub 33 to retract into the hollow cone 11, until the trailing end of the hub 33 becomes wedge impacted 41 in the trailing bore of the hollow cone 11. It will be found that the slant of the leading aperture 13 of the hollow cone 11, combined with the flexion or extension angle 31 of the proximal end of the tether 12 will provide good alignment for painless withdrawal of the needle 32; and also insure that the needle hub 33 slides back in contact with the dorsal bore of the tether 12 and hollow cone 11, thus preventing hang-up of the ventral portion of the needle hub 33 on entry into the leading slanted aperture 13. After the needle hub 33 is wedge impacted 41, and the shaft 32 and sharp tip 91 of the needle are safely housed within the leading confines of the hollow cone 11, the user should maintain pressure 81 over the venipuncture site until the likelihood of bleeding subsides. Then, pressure can be released and a bandage placed over the pledget. The hollow cone 11 containing the safely shielded needle 32 can, then, be disposed into a sharps container. Preferably, if disposal is not immediate, the original needle sheath supplied with the IV access needle should be replaced over the needle to avoid blood drippage. This re, sheathing of the needle with its original protective sheath 103 will be found simple and safe, because the leading slanted aperture 13 of the hollow cone will normally allow easy entry of a standard needle sheath, but not the tip of a finger, provided that the hub 33 of the IV access needle 32 is not too large in greatest external diameter.

Operation of the third preferred embodiment varies only in that the user must attach the tethered hollow conical shield 11, before inserting the phlebotomy needle 32 into a vein. It will be appreciated by those skilled in the current art, as well as prior, that wide variations in details and materials can be made without departure from the spirit of this invention.

Therefore, I claim:

1. A shield for safely enclosing a hollow-bore steel needle, said needle having a round or rectangular needle hub which is affixed to trailing tubing, said shield comprising:
   a. a hollow cone with a slanted leading aperture whose smallest internal diameter exceeds the greatest external diameter of said needle hub, a trailing aperture whose internal diameter approximately equals the external diameter of said trailing tubing, and a conical cavity whose length between said slanted leading aperture and said trailing aperture is substantially longer than the combined axial length of said hollow-bore steel needle and said needle hub; and
   b. a tether having an expanded leading portion and a flexible trailing portion affixed to the leading portion of said hollow cone.

2. Said hollow cone, as in claim 1, further comprising a conical body portion wherein the consistency is either less rigid than that of said needle hub, or more rigid, at a point of wedge impaction where the internal diameter of said hollow cone becomes less than the greatest external diameter of said needle hub.

3. Said hollow cone, as in claim 1, further comprising an affixed tether wherein said trailing flexible portion can flex in arc approaching 135° over said slanted leading aperture, and said expanded leading portion has a roughened dorsal surface.

4. Said hollow cone, as in claim 1, further comprising a consistency which is resistant to puncture by a sharp tip on said hollow bore steel needle and is, preferably, optically transparent.

5. Said hollow cone, as in claim 1, further comprising, in a second preferred embodiment, a slot between the trailing end of said slanted leading aperture and the frustum of said trailing aperture, said slot being of sufficient width to permit passage therethrough of said trailing tubing affixed to said needle hub.

6. Said hollow cone, as in claim 1, further comprising, in a third preferred embodiment, said trailing aperture wherein said internal diameter is larger than the greatest external diameter of a flange on a trailing hub permanently affixed to said trailing tubing and smaller than said greatest external diameter of said needle hub.

* * * * *